US006605597B1

(12) United States Patent
Zablocki et al.

(10) Patent No.: US 6,605,597 B1
(45) Date of Patent: Aug. 12, 2003

(54) PARTIAL OR FULL A₁ AGONISTS-N-6 HETEROCYCLIC 5'-THIO SUBSTITUTED ADENOSINE DERIVATIVES

(75) Inventors: Jeff A. Zablocki, Mountain View, CA (US); Venkata P. Palle, Mountain View, CA (US); Vaibhav Varkhedkar, Sunnyvale, CA (US); Luiz Belardinelli, Menlo Park, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/454,136

(22) Filed: Dec. 3, 1999

(51) Int. Cl.⁷ .......................... A61K 51/70; C07H 19/16
(52) U.S. Cl. ........................................ 514/46; 536/27.3
(58) Field of Search ............................ 514/46; 536/27.3

(56) References Cited

U.S. PATENT DOCUMENTS

| 4,373,097 A | | 2/1983 | Stramentinoli et al. ... 536/27.62 |
| 5,589,467 A | | 12/1996 | Lau et al. .................. 514/46 |
| 5,789,416 A | * | 8/1998 | Lum et al. .................. 514/261 |
| 6,258,793 B1 | * | 7/2001 | Palle et al. ................. 514/46 |
| 6,294,522 B1 | * | 9/2001 | Zablocki et al. ............ 514/46 |

FOREIGN PATENT DOCUMENTS

| WO | WO 99/24450 A2 | * | 5/1999 |
| WO |     9924450    | * | 5/1999 |
| WO | WO 99/24451 A2 | * | 5/1999 |
| WO |     9924451    | * | 5/1999 |

OTHER PUBLICATIONS

Hutchinson et al., "Adenosine Receptor Ligands with Oxygenated N⁶–Substituents," *Bioorganic & Medicinal Chemistry Letters*, 9(7), 933–936 (Apr. 5, 1999).*

Snowdy et al., "A Comparison of an A₁ Adenosine Receptor Agonist (CVT–510) with Diltiazem for Slowing of AV Nodal Conduction in Guinea–Pig," *British Journal of Pharmacology*, 126(1), 137–146 (1999). month unavailable.*

B. Lerman et al, "Cardiac Electrophysiology of Adenosine", *Circulation*, vol. 83 (1991) p. 1499–1509 (May, 1991).

J.C. Shryock, "Adenosine and Adenosine Receptors in the Cardiovascular System: Biochemistry, Physiology, and Pharmacology", *The Am. J. Cardiology*, vol. 79 (1997) p. 2–10 (Jun. 19, 1997).

J.D. Thornton, "Intravaneous Pretreatment with A₁–Selective Adenosine Analogues Protects the Heart Against Infarction", *Circulation*, vol. 85 (1992), p. 659–665 (Feb., '92).

E. A. van Schaick et al., "Physiological Indirect Effect Modeling of the Antipolytic Effects of Adenosine A₁–Receptor Agonists", *Pharmacokinetics and Biopharmaceutics*, vol. 25, (1997) p. 673–694.

P. Strong, "Suppression of non–esterified fatty acids and triacylglycerol in experimental animals by the adenosine analogue GR79236", *Clinical Science*, vol. 84 (1993), p. 663–669. month unavailable.

D. Thiebaud et al, "Effects of Long Chain Triglyceride Infusion on Glucose Metabolism in Man", *Metab. Clin. Exp.*, vol. 31 (1982), p. 1128–1136 (Nov., 1982).

G. Boden et al., "Mechanism of Fatty–Acid–Induced Inhibition of Glucose Uptake", *J. Clin. Invest.*, vol. 93, (1994) p. 2438–2446 (Jun., 1994).

P.J. Randle et al., "The Glucose Fatty–Acid Cycle Its Role in Insulin Sensitivity and the Metabolic Disturbances of Diabetes Mellitus", *Lancet* (1963) p. 785–789 (Apr. 13, 1963).

Klitgaard, et al., "Contrasting Effects of Adenosine A₁ and A₂ Receptor Ligands in Different Chemoconvulsive Rodent Models," *Eur. J. Pharmacol* (1993), vol. 224, pp. 221–228. month unavailable.

G. Zhang, "Activation of adenosine A1 receptors underlies anticonvulsant effect of CGS21680", *Eur. J. Pharmacol*, vol. 255 (1994), p. 239–243. month unavailable.

Knutsen, "N–Substituted Adenosines as Novel Neuroprotective A1 Agonists with Diminished Hypotensive Effect", *J. Med. Chem.*, vol. 42 (1999) p. 3463–3477 (No. 18). month unavailable.

Vergauwen, et al., "Adenosine Receptors Mediate Synergistic Stimulation of Glucose Uptake and Transport by Insulin and by Contractions in Rat Skeletal Muscle", *J. Clin. Invest*, (1994) 93, 974–81 (Mar., 1994).

Gellai, et al., "CVT–124, a Novel Adenosine A1 Receptor Antagonist with Unique Diuretic Activity", *JPET*, (1998) 286, p. 1191–1196 (Issue No. 3) J. Pharm. Expt. Therap.

Wilcox, et al., "Natriuretic and Diuretic Actions of a Highly Selective Adenosine A₁ Receptor Anagonist," *J. Am. Soc. Nephrol*, (1999) 10, p. 714–720. month unavailable.

R.B. Clark, et al., "Partial agonists and G protein–coupled receptor desensitization", *TiPS*, vol. 20 (1999), p. 279–286 (Jul., 1999).

D. M. Dennis et al., "Homologous Desensitization of the A1–Adenosine Receptor System in the Guinea Pig Atrioventricular Node," *JPET*, vol. 272 (1995), p. 1024–1035 (No. 3). month unavailable.

Parsons, J., "Heterologous Densitization of the Inhbitory A1 Adenosine Receptor–(Adenylate Cyclase System in Rat Adipocytes", *Biol. Chem.* vol. 262 (1987) p. 841–847 Jan. 15, 1987. month unavailable.

(List continued on next page.)

Primary Examiner—James O. Wilson
Assistant Examiner—L. Eric Crane
(74) Attorney, Agent, or Firm—McDonnell Boehnen Hulbert & Berghoff

(57) ABSTRACT

N⁶ heterocyclic 5' modified adenosine derivatives that are adenosine A₁ receptor partial or full agonists, and as such, are useful for modifying cardiac activity, modifying adipocyte function, treating central nervous system disorders, and treating diabetic disorders and obesity in mammals, and especially in humans.

13 Claims, No Drawings

OTHER PUBLICATIONS

Lerman et al., "Electrophysiologic Effects of a Novel Selective Adenosine $A_1$ Agonist (CVT–510) on Atrioventricular Nodal Conduction in Humans," *Journal of Cardiovasc. Pharmacol. Therapeut.,* 6(3), 237–245 (2001) month unavailable.*

Cheng et al., "Activation of Adenosine $A_1$ Receptors by Drugs to Lower Plasma Glucose in Streptozotocin–Induced Diabetic Rats," *Autonomic Neuroscience: Basic and Clinical,* 83, 127–133 (2000) month unavailable.*

Vannucci et al., "$A_1$ –Adenosine Receptor–Mediated Inhibition of Adipocyte Adenylate Cyclase and Lipolysis in Zucker Rats," *American Journal of Physiology,* 257 (*Endocrinol. Metab., 20*), E871–878 (1989) month unavailable.

Von Lubitz et al., "Protection Against Ischemic Damage by Adenosine Amine Congener, a Potent and Selective Adenosine $A_1$ Receptor Agonist," *European Journal of Pharmacology,* 369, 313–317 (1989) month unavailable.

Tommasi et al., "Low–Dose Dipyridamole Infusion Acutely Increases Exercise Capacity in Angina Pectoris—A Double–Blind, Placebo Controlled Crossover Stress Echocardiographic Study," *J. American College of Cardiology,* 35(1), 83–88 (Jan., 2000).

Louttit et al., "The Time Course of Cardioprotection Induced by GR79236, A Selective Adenosine $A_1$ –Receptor Agonist, in Myocardial Ischaemia–Reperfusion Injury in the Pig," *Journal of Cardiovascular Pharmacology,* 33(2), 285–291 (1999). month unavailable.

L. Carroll, "Mounting Data on Epilepsy Points to Dangers of Repeated Seizures," *The New York Times, Sec. D* (Science Times), pp. D5 and D8, Feb. 18, 2003.

* cited by examiner

PARTIAL OR FULL $A_1$ AGONISTS-N-6 HETEROCYCLIC 5'-THIO SUBSTITUTED ADENOSINE DERIVATIVES

BACKGROUND OF THE INVENTION

(1) Field of the Invention

This invention includes stable and useful drugs and pro-drugs that are $N^6$ heterocyclic 5'-thio modified adenosine derivatives. The compositions of this invention are selective, partial or full adenosine $A_1$ receptor agonists, and as such, are useful for modifying cardiac activity, modifying adipocyte function, treating central nervous system disorders, and treating diabetic disorders and obesity in mammals, and especially in humans.

(2) Description of the Art

There are at least two subtypes of adenosine receptors in the heart: $A_1$ and $A_{2A}$. Each subtype affects different physiological functions. The $A_1$ adenosine receptor mediates two distinct physiological responses. Inhibition of the cardiostimulatory effects of catecholamine are mediated via the inhibition of adenylate cyclase, whereas the direct effects to slow the heart rate (HR) and to prolong impulse propagation through the AV node are due in great part to activation of $I_{KAdo}$. (B. Lerman and L. Belardinelli Circulation, Vol. 83 (1991), P 1499–1509 and J. C. Shryock and L. Belardinelli The Am. J. Cardiology, Vol. 79 (1997) P 2–10). Both, the anti-β-adrenergic action and direct depressant effects on SA and AV nodal function are mediated by the $A_1$ receptor; there is no role for the $A_{2A}$ receptor in this response to adenosine. $A_{2A}$ receptors mediate the coronary vasodilatation caused by adenosine. Stimulation of the $A_1$ adenosine receptor accordingly shortens the duration and decreases the amplitude of the action potential of AV nodal cells, and hence prolongs the refractory period of the AV nodal cell. The consequence of these effects is to limit the number of impulses conducted from the atria to the ventricles. This forms the basis of the clinical utility of $A_1$ receptor agonists for the treatment of supraventricular tachycardias, including termination of nodal re-entrant tachycardias, and control of ventricular rate during atrial fibrillation and flutter.

A clinical utility of $A_1$ agonists therefore is in the treatment of acute and chronic disorders of heart rhythm, especially those diseases characterized by rapid heart rate where the rate is driven by abnormalities in the sinoatrial, atria, and AV nodal tissues. Such disorders include but are not limited to atrial fibrillation, supraventricular tachycardia and atrial flutter. Exposure to $A_1$ agonists causes a reduction in the heart rate and a regularization of the abnormal rhythm thereby improving cardiovascular function.

$A_1$ agonists, through their ability to inhibit the effects of catecholamines, decrease cellular cAMP, and thus, should have beneficial effects in the failing heart where increased sympathetic tone increases cellular cAMP levels. The latter has been shown to be associated with increased likelihood of ventricular arrhythmias and sudden death. All of the above concepts are discussed in reviews regarding the effects of adenosine on cardiac electrophysiology (see B. Lerman and L. Belardinelli Circulation, Vol. 83 (1991), P 1499–1509 and J. C. Shryock and L. Belardinelli, Am. J. Cardiology, Vol. 79 (1997) P 2–10).

A controversial area in the field of $A_1$ adenosine agonism is that the benefit of preconditioning of the heart prior to ischemia may be due to binding of adenosine to the $A_1$ receptor. Evidence for this hypothesis comes from a rabbit ischemia model wherein 2-chloro-N6-cyclopentyladenosine (CCPA) and R-PIA were administered prior to ischemia providing protection with respect to infarct size (J. D. Thornton et al. Circulation Vol. 85 (1992) 659–665).

$A_1$ agonists, as a result of their inhibitory action on cyclic AMP generation, have antilipolytic effects in adipocytes that leads to a decreased release of nonesterified fatty acids (NEFA) (E. A. van Schaick et al J. Pharmacokinetics and Biopharmaceutics, Vol. 25 (1997) p 673∫694 and P. Strong Clinical Science Vol. 84 (1993) p. 663–669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al Metab. Clin. Exp. Vol. 31 (1982) p 1128–1136 and G. Boden et al J. Clin. Invest. Vol. 93 (1994) p 2438–2446). The hypothesis of a glucose fatty acid cycle was proposed by P. J. Randle as early as 1963 (P. J. Randle et al Lancet (1963) p. 785–789). A tenet of this hypothesis would be that limiting the supply of fatty acids to the peripheral tissues should promote carbohydrate utilization (P. Strong et al Clinical Science Vol. 84 (1993) p. 663–669).

The benefit of an $A_1$ agonist in central nervous disorders has been reviewed and the content are included herein by reference (L. J. S. Knutsen and T. F. Murray In Purinergic Approaches in Experimental Therapeutics, Eds. K. A. Jacobson and M. F. Jarvis (1997) Wiley-Liss, N. Y., P -423–470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard Eur. J. Pharmacol. (1993) Vol. 224 p. 221–228). In other studies using CGS 21680, an $A_{2A}$ agonist, it was concluded that the anticonvulsant activity was attributed to activation of the $A_1$ receptor (G. Zhang et al. Eur. J. Pharmacol. Vol. 255 (1994) p. 239–243). Furthermore, $A_1$ adenosine selective agonists have been shown to have anticonvulsant activity in the DMCM model (L. J. S. Knutsen In Adenosine and Adenne Nucleotides: From Molecular Biology to Integrative Physiology; eds. L. Belardinelli and A. Pelleg, Kluwer: Boston, 1995, pp 479–487). A second area where an $A_1$ adenosine agonist has a benefit is in animal models of forebrain ishemia as demonstrated by Knutsen et al (J. Med. Chem. Vol. 42 (1999) p. 3463–3477). The benefit in neuroprotection is believed to be in part due to the inhibition of the release of excitatory amino acids (ibid).

There are a number of full $A_1$ agonists disclosed in the prior art. However, the agonists disclosed are generally in the forms that are not useful in the mammalian body. Because useful forms of $A_1$ agonists may not always be stable, soluble or they may have other properties that make their incorporation into therapeutic dosage forms difficult, it is often necessary to identify compositions that are more easily incorporated into therapeutic dosage forms in order to provide the desired therapeutic effect. Also, these agonists fail as useful therapeutics due to side effects caused by the non-selective stimulation of the $A_1$ adenosine receptor in all biologically available tissues and the desensitization of the desired response preempting their use as chronic agents. Therefore, there remains a need for specific and selective $A_1$ agonists, precursors and/or pro-drugs that are converted in the body into useful therapeutic compositions.

SUMMARY OF THE INVENTION

In one aspect, this invention includes heterocyclic 5'-thio modified adenosine derivative compositions that are useful partial or full adenosine $A_1$ receptor agonists.

In another aspect, this invention includes pharmaceutical compositions including one or more heterocyclic 5'-thio modified adenosine derivative compositions that are well tolerated with few side effects.

In still another embodiment, this invention includes heterocyclic 5'-thio modified adenosine derivatives having the formula:

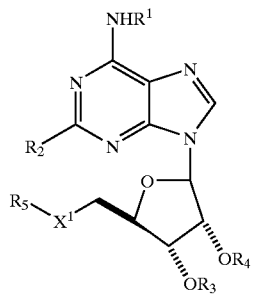

In yet another embodiment, this invention includes methods for administering compositions of this invention to mammals, and especially to humans, to stimulate coronary activity, to modify adipocyte function, to treat central nervous system disorders, and to treat diabetic disorders.

In a further embodiment, this invention is pharmaceutical compositions of matter comprising at least one composition of this invention and one or more pharmaceutical excipients.

DESCRIPTION OF THE CURRENT EMBODIMENT

This invention includes a class of heterocyclic 5'-thio modified adenosine derivatives having the formula having the formula:

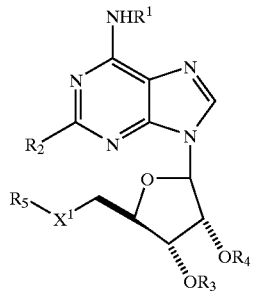

wherein $X^1$=S, S(O), S(O2);

wherein $R^1$ is a monocyclic or polycyclic heterocyclic group containing from 3 to 15 carbon atoms wherein at least one carbon atom is substituted with an atom or molecule selected from the group consisting of N, O, P and S—$(O)_{0-2}$ and wherein $R^1$ does not contain an epoxide group, and wherein $R_2$ is selected from the group consisting of hydrogen, halo, $CF_3$, and cyano; wherein $R_3$ and $R_4$ are independently selected from the group consisting of hydrogen, and —(CO)—R' and —(CO)—R" wherein R' and R" are independently selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl, and heteroaryl are optionally substituted with 1 to 3 substituents independently selected from the group of halo, $NO_2$, heterocyclyl, aryl, heteroaryl, $CF_3$, CN, $OR^{20}$, $SR^{20}$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and each optional heteroaryl, aryl, and heterocyclyl substituent is optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

wherein $R_5$ is selected from the group consisting of $C_{1-15}$ alkyl, $C_{2-15}$ alkenyl, $C_{2-15}$ alkynyl, heterocyclyl, aryl, and heteroaryl, wherein alkyl, alkenyl, alkynyl, aryl, heterocyclyl, and heteroaryl are optionally substituted with 1 to 3 substituents independently selected from the group consisting of halo, alkyl, $NO_2$, heterocyclyl, aryl, heteroaryl, $CF_3$, CN, $OR^{20}$, $SR^{20}$, $S(O)_3R^{20}$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $P(O)(OR^{20})_2$, $N(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein optional heteroaryl, aryl, and heterocyclyl substituent is optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

wherein $R^{20}$ is a member selected from the group consisting of H, C1–15 alkyl, C2–15 alkenyl, C2–15 alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, mono- or dialkylamino, alkyl or aryl or heteroaryl amide, CN, O—C1–C6 alkyl, CF3, aryl, and heteroaryl; and $R^{22}$ is a member selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, mono- or dialkylamino, alkyl or aryl or heteroaryl amide, CN, O—$C_{1-6}$ alkyl, $CF_3$, and heteroaryl.

In preferred compositions, $X^1$=S or $SO_2$; $R_2$ is a hydrogen; $R_3$ and $R_4$ are each independently selected from the group consisting of hydrogen, —(CO)—R' and —(CO)—R" wherein R' and R" are each independently selected from the group consisting of $C_{1-6}$ alkyl and, more preferably, $R_3$ and $R_4$ are each hydrogen; $R_5$ is selected from the group consisting of $C_{1-8}$ alkyl, and aryl wherein alkyl, and aryl are optionally substituted with from 1 to 2 substituents independently selected from the group consisting of halo, alkyl, aryl, heteroaryl, $CF_3$, CN, $OR^{20}$, $S(O)R^{22}$, $SO_2R^{22}$, $SO_2N(R^{20})_2$, $NR^{20}CON(R^{20})_2$, $CO_2R^{20}$, $CON(R^{20})_2$, and wherein each optional heteroaryl, and aryl substituent is further optionally substituted with halo, alkyl, $CF_3$, $CO_2R^{20}$, CN, and $OR^{20}$; $R_{20}$ is selected from the group consisting of H, $C_{1-6}$ alkyl; and $R_{22}$ is selected from the group consisting of $C_{1-6}$. In the above compositions, $R_5$ is more preferably selected from the group consisting of $C_{1-8}$ alkyl, and aryl wherein alkyl, and aryl are optionally substituted with from 1 to 2 substituents independently selected from the group consisting of halo, alkyl, $CF_3$, and $OR^{20}$.

In more preferred compositions, $X^1$=S or $SO_2$; $R_2$ is a hydrogen; $R_3$ and $R_4$ are independently selected from the group consisting of hydrogen, —(CO)—R' and —(CO)—R" wherein R' and R" are each independently selected from the group consisting of $C_{1-16}$ alkyl which alkyl are optionally substituted with 1 substituent selected from the group consisting of aryl, $CF_3$, CN, $OR^{20}$, $N(R^{20})_2$, and wherein each optional aryl substituent is further optionally substituted with halo, $NO_2$, alkyl, $CF_3$; $R_5$ is $C_{1-8}$ alkyl, wherein alkyl, is optionally substituted with from 1 to 2 substituents independently selected from the group consisting of halo, alkyl, aryl, heteroaryl, $CF_3$, CN, $OR^{20}$, $S(O)R^{22}$, $SO_2R^{22}$, $SO_2N(R^{20})_2$, $NR^{20}CON(R^{20})_2$, $CO_2R^{20}$, $CON(R^{20})_2$, wherein each optional heteroaryl, and aryl substituent is further optionally substituted with halo, alkyl, $CF_3$, $CO_2R^{20}$, CN, and $OR^{20}$; $R^{20}$ is selected from the group consisting of H, $C_{1-6}$ alkyl; and $R_{22}$ is selected from the group consisting of $C_{1-6}$. In the above compositions, $R_5$ is more preferably $C_{1-8}$ alkyl that is optionally substituted with from 1 to 2 substituents independently selected from the group consisting of aryl, heteroaryl, $OR^{20}$, $S(O)R^{22}$, $CO_2R^{20}$, $CON(R^{20})_2$, and wherein each optional heteroaryl, and aryl substituent is further optionally substituted with halo, alkyl, $CF_3$, $CO_2R^{20}$, CN, and $OR^{20}$, and $R_5$ is even more preferably $C_{1-8}$ alkyl that is optionally substituted with 1 substituent selected from the group consisting of $CO_2R^{20}$, and $CON(R^{20})_2$, and $R_5$ is even more preferably $C_{1-6}$ alkyl and most preferably methyl or ethyl or isopropyl. Also in the above compositions, $R_3$ and $R_4$ are more preferably each hydrogen and $R_{20}$ is more preferably selected from the group consisting of H, and methyl.

In another class of preferred compositions, $R_2$ is a hydrogen; $R_3$ and $R_4$ are each independently selected from the group consisting of hydrogen,—(CO)—R' and —(CO)—R" wherein each R' and R" are independently selected from the group consisting of $C_{1-6}$ alkyl, and aryl, which alkyl and aryl are optionally substituted with from 1 to 2 substituents independently selected from the group of halo, $NO_2$, aryl, $CF_3$, CN, $OR^{20}$, $N(R^{20})_2$, $S(O)R^{22}$, $SO_2R^{22}$, wherein each optional aryl substituent is further optionally substituted with halo, $NO_2$, alkyl, $CF_3$; $R_5$ is selected from the group consisting of, aryl, and heteroaryl, wherein aryl, and heteroaryl are optionally substituted with from1 to 3 substituents independently selected from the group consisting of halo, alkyl, aryl, heteroaryl, $CF_3$, CN, $OR^{20}$, $SR^{20}$, $N(R^2)_2$, $S(O)R^{22}$, $SO_2R^{22}$, $SO_2N(R^{20})_2$, $NR^{20}CO_2R^{22}$, $NR^{20}CON(R^{20})_2$, $CO_2R^{20}$, $CON(R^{20})_2$, and wherein each optional heteroaryl, and aryl substituent is further optionally substituted with halo, alkyl, $CF_3$, $CO_2R^{20}$, $CON(R^{20})_2$, $S(O)R^{22}$, $SO_2R^{22}$, $SO_2N(R^{20})_2$, CN, or $OR^{20}$; $R^{20}$ is selected from the group consisting of H, $C_{1-6}$ alkyl, and aryl, which alkyl and aryl are optionally substituted with 1 substituent selected from halo, alkyl, mono- or dialkylamino, CN, O—$C_{1-6}$ alkyl, $CF_3$; and $R^{22}$ is selected from the group consisting of $C_{1-6}$ alkyl and aryl, which alkyl and aryl are optionally substituted with 1 substituent selected from halo, alkyl or CN, O—$C_{1-6}$ alkyl, and $CF_3$. In the above compositions, $X^1$ is preferably S; $R_3$ and $R_4$ are more preferably hydrogen; $R_5$ is more preferably selected from the group consisting of, aryl, and heteroaryl, wherein aryl, and heteroaryl are optionally substituted with from 1 to 3 substituents independently selected from the group consisting of halo, alkyl, $CF_3$, CN, $OR^{20}$, $SR^{20}$, $CO_2R^{20}$, $CON(R^{20})_2$. Even more preferably $R_5$ is aryl that is optionally substituted with from 1 to 2 substituents independently selected from the group consisting of halo, alkyl, $CF_3$, $OR^{20}$, $CO_2R^{20}$, $CON(R^{20})_2$. And most preferably, $R_5$ is phenyl that is optionally substituted with a substituent selected from the group consisting of methoxy, chloro, fluoro, methyl, and trifluoromethyl. In the compounds above, $R^{20}$ is preferably selected from the group consisting of H, $C_{1-3}$ alkyl and most preferably H or methyl while $R_{22}$ is preferably selected from the group consisting of $C_{1-6}$ alkyl.

In the compositions of this invention, $R_1$ is preferably mono or polysubstituted with one or more compounds selected from the group consisting of halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof. More preferably, $R_1$ is a monocyclic, bicyclic, or tricyclic cycloalkyl group containing from 3 to 15 carbon atoms wherein at least one carbon atom is substituted with an atom or molecule selected from the group consisting of O or S—$(O)_{0-2}$. Some examples of preferred $R_1$ moieties include:

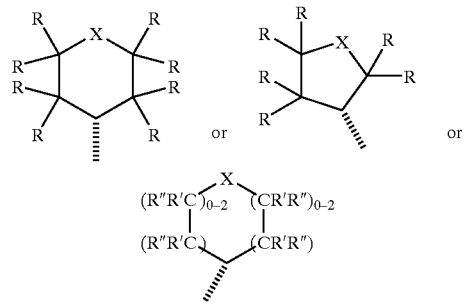

wherein R' and R" may each individually be selected from the group halogen, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, and cyano, and X is O, or S$(—O)_{0-2}$, alternately, CR'R" may be C=O. More preferably, R' and R" are each individually selected from the group hydrogen, lower alkyl, and substituted lower alkyl. In the compositions above, each R is individually selected from the group consisting of H, lower alkyl, and substituted lower alkyl.

Most preferred compounds of this invention include, 2-{6-[((3R)oxolan-3-yl)amino]purin-9-yl}(4S,5S,2R,3R)-5-(methylthiomethyl)oxolane-3,4-diol; 2-{6-[((3R)oxolan-3-yl)amino]purin-9-yl}(4S,5S,2R,3R)-5-[(Ethylthio)methyl]oxolane-3,4-diol; 2-{6-[((3R)oxolan-3-yl)amino]purin-9-yl}(4S,5S,2R,3R)-5-[(Methylethylthio)methyl]oxolane-3,4-diol; 2-{6-[((3R)oxolan-3-yl)amino]purin-9-yl}(4S,5S,2R,3R)-5-(phenylthiomethyl)oxolane-3,4diol; 2-{6-[((3R)oxolan-3-yl)amino]purin-9-yl}(4S,5S,2R,3R)-5-[(4-Methoxyphenylthio)methyl]oxolane-3,4-diol; 2-{6-[((3R)oxolan-3-yl)amino]purin-9-yl}(4S,5S,2R,3R)-5-[(4-chlorophenylthio)methyl]oxolane-3,4-diol; 2-{6-[((3R)oxolan-3-yl)amino]purin-9-yl}(4S,5S,2R,3R)-5-[(4-fluorophenylthio)methyl]oxolane-3,4-diol; 2-{6-[((3R)oxolan-3-yl)amino]purin-9-yl}(4S,5S,2R,3R)-5-[(4-methylphenylthio)methyl]oxolane-3,4-diol; 2-{6-[((3R)oxolan-3-yl)amino]purin-9-yl}(4S,5S,2R,3R)-5-[(4-(trifluoromethyl)phenylthio)methyl]oxolane-3,4-diol; 2-{6-[((3R)oxolan-3-yl)amino]purin-9-yl}(4S,5S,2R,3R)-5-[(2-methoxyphenylthio)methyl]oxolane-3,4-diol; and (5-{6-[((3R)oxolan-3-yl)amino]purinyl-9-yl}(2S,3S,4R,5R)-3,4-dihydroxyoxolan-2-yl)(ethylsulfonyl)methane.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4 carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'"R"", where R is lower alkyl, or substituted lower alkyl, R', R'", R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1\text{-}2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O, P, or S—(O)$_{0-2}$, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R—Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds of this invention can be prepared as outlined in the schemes 1–5 below. A general outline for the preparation of V and VI is shown in Scheme 1. Compound I can be prepared, following the procedures reported earlier (U.S. Pat. No. 5,789,416, the specification of which is incorporated herein by reference), by reacting 6-chloropurine riboside 1 with a primary amine R$^1$NH$_2$. The 2', 3' hydroxy groups can be protected as acetonide by reacting I with 2,2'-dimethoxypropane in the presence of a catalytic amount of TsOH [Evans, Parrish and Long Carbohydrat. Res., 3,453 (1967)] to give II. Activation of the 5'-hydroxyl of II with MsCl in pyridine can give the 5'-mesylate III. Displacement of the 5'-mesylate with R$^5$SNa can give sulfides with the general formula IV. Treatment of IV with an acid can free the 2', 3' hydroxyl groups to give sulfide derivatives with the general formula V. Esterification of V can afford 2', 3' diesters with the general formula VI.

Scheme 1

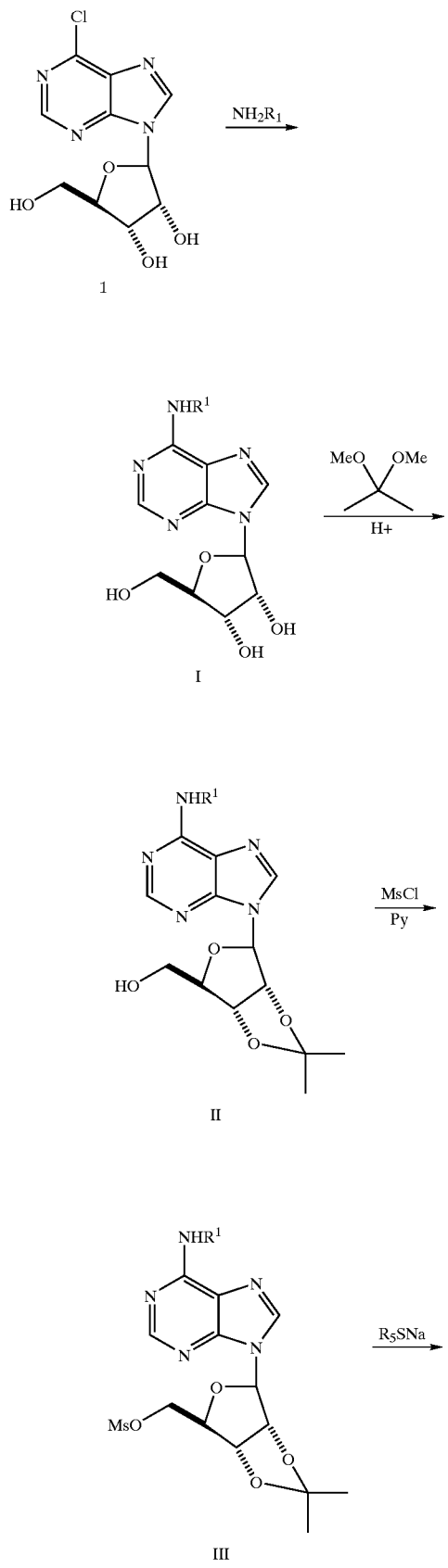
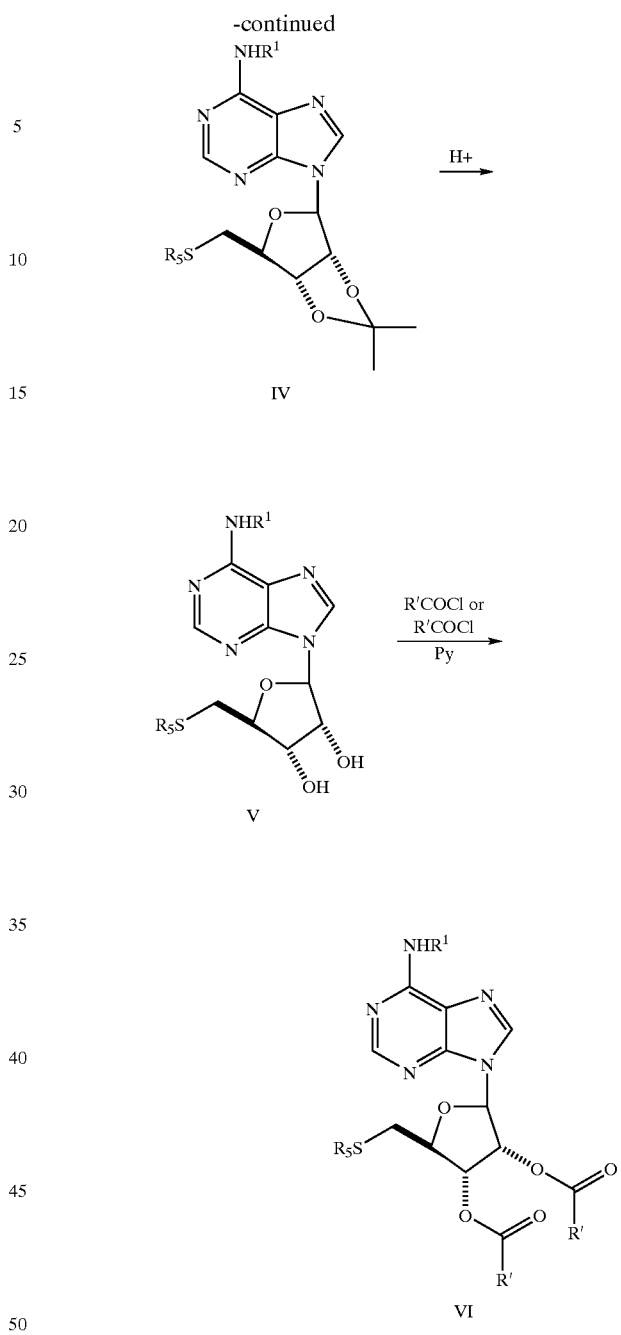

The 2-substituted derivatives with the general formula XV can be prepared as shown in Scheme 2. Condensation of 1,2,3,5-tetraacetylribofuranaside 2 with 2-substituted-6-chloropurine VII can give 2-substituted-6-chloropurineriboside triacetate VIII which on reaction with a primary amine $R^1NH_2$ can give 2-substituted-6-alkylamino derivatives IX. Hydrolysis of the acetates followed by protection of the 2', 3' hydroxy groups as an acetonide can give XI. Activation of the 5'-hydroxyl of XI with MsCl in pyridine can give the 5'-mesylate XII. Displacement of the 5'-mesylate with $R^5SNa$ can give sulfides with the general formula XIII that can be deprotected to give sulfides with general formula XIV.

Scheme 2
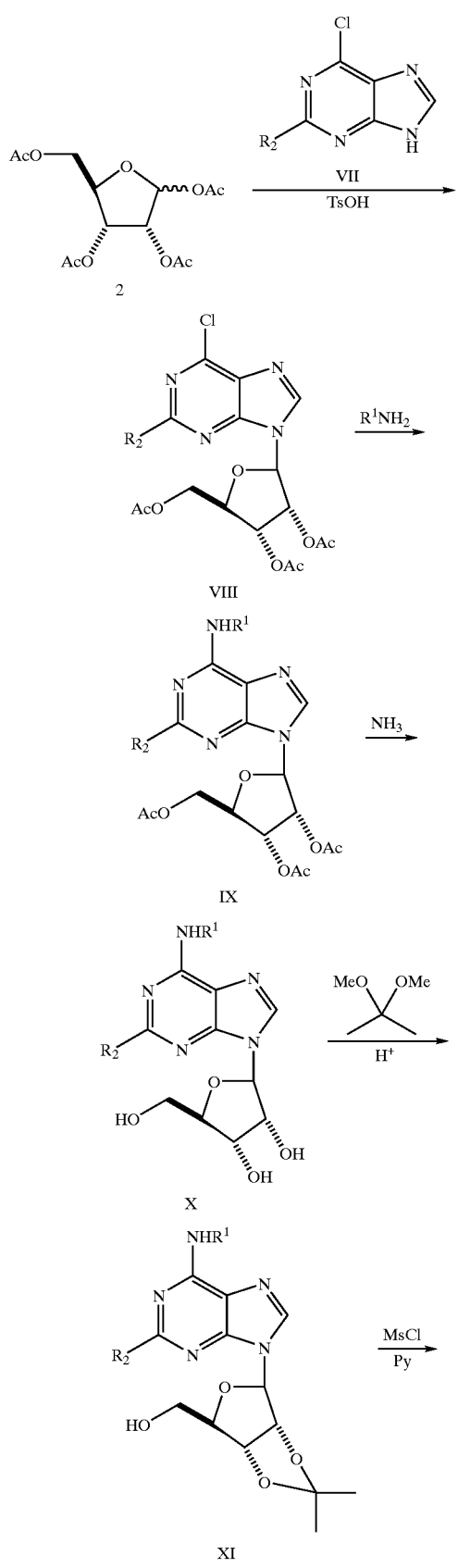
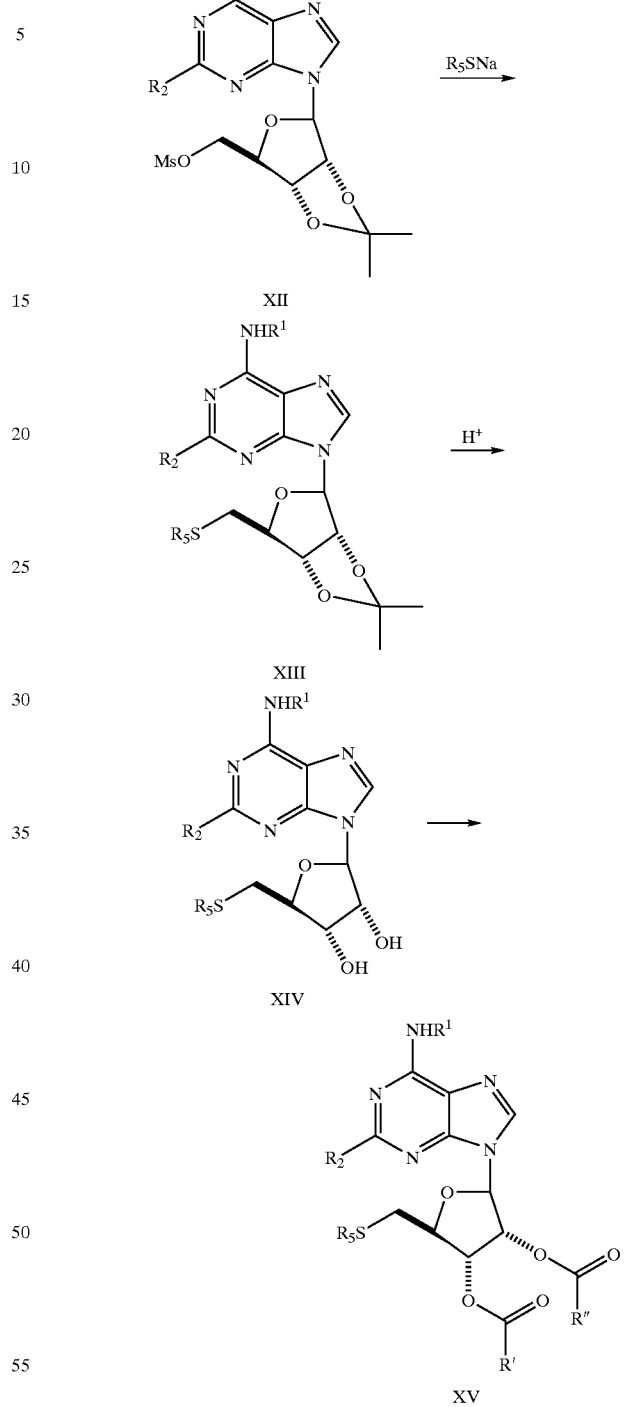
Oxidation of sulfides with the general formula V, VI, XIV, XV (Scheme 3) with an oxidizing agent (Drabowicz, et.al. The chemistry of sulfones and sulfoxides, Wiley, N.Y., 1988, 233–378) can afford corresponding sulfoxides with the general formula XVI, XVII, XVIII, XIX. These sulfoxides on further oxidation can afford sulfones with the general formula XX, XXI, XXII, XXIII.

Scheme 3
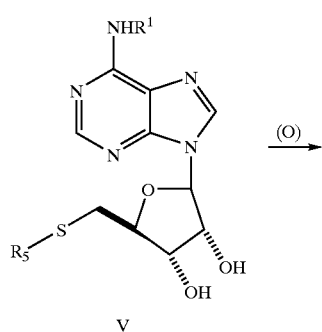
V
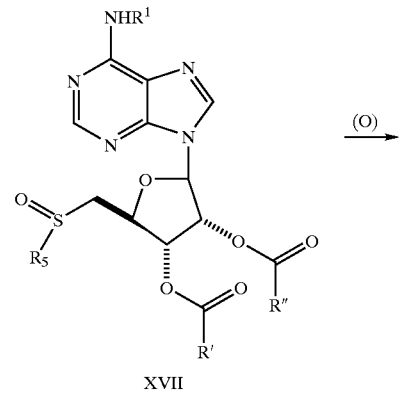
XVII
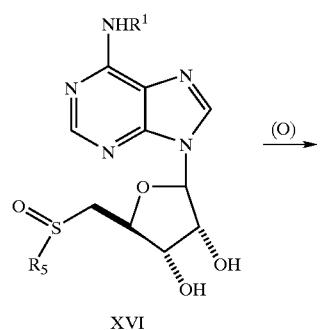
XVI
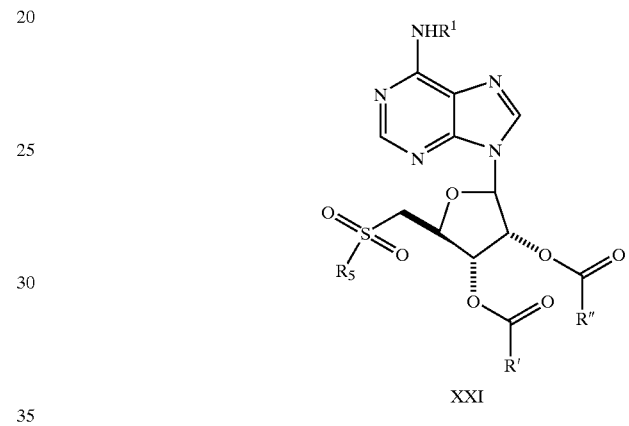
XXI
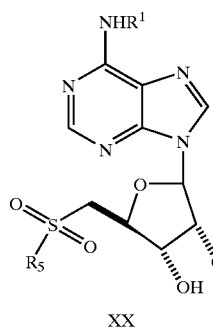
XX
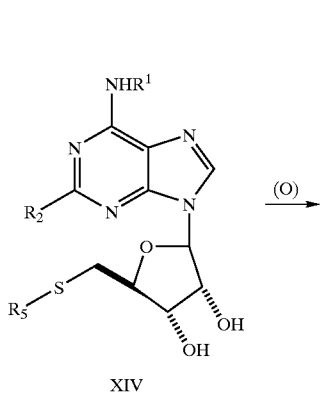
XIV
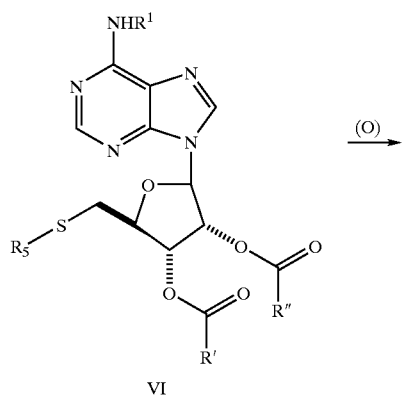
VI
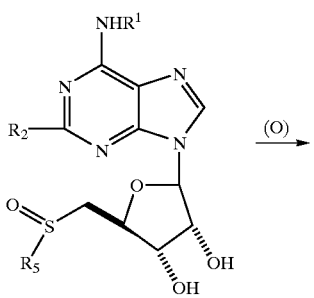
XVIII

Scheme 4

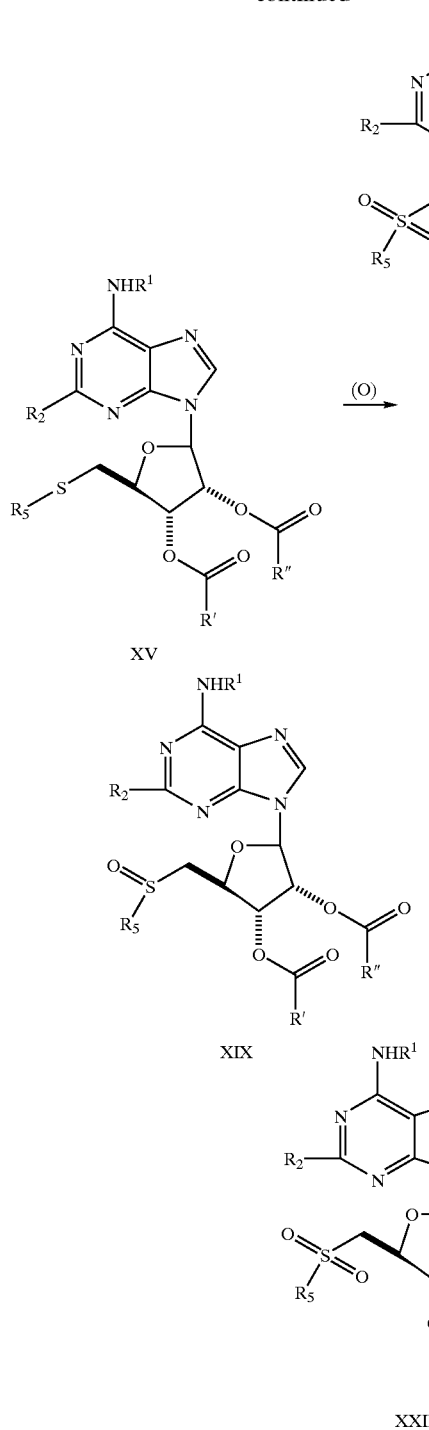

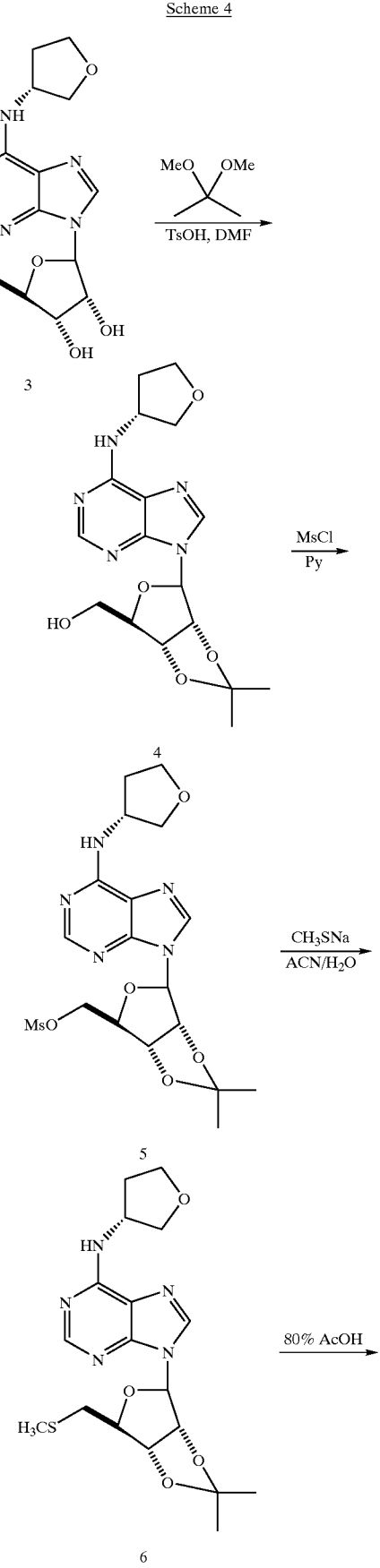

An example of a specific synthesis of one of the compounds of this invention is shown in Scheme 4. Preparation of compound 7 starting from compound 3 is shown in scheme 3. Compound 3 was prepared from 6-chloropurineriboside 1 and 3-(R)-aminotetrahydrofuran following the procedure reported previously (See U.S. Pat. No. 5,789,164). Protection of the 2' and 3' hydroxyls with dimethoxypropane in the presence of TsOH(cat.) gave acetonide 4. Reaction of 4 with MsCl in pyridine at 0° C. gave mesylate 5 which on displacement with sodium methanethiolate in an acetonitrile/water mixture gave sulfide 6. Deprotection of 6 with 80% acetic acid/water gave the target compound 7.

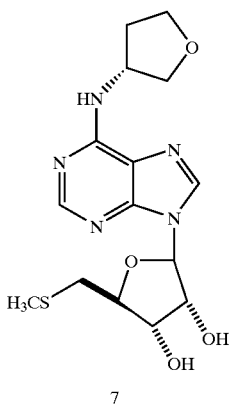

7

Oxidation of the ethyl sulfide 8 with oxone (Trost, B. M.; Curran, D. P. Tetrahedron Letters 1981, 22, 1287) in MeOH gave sulfone 9 (Scheme 5).

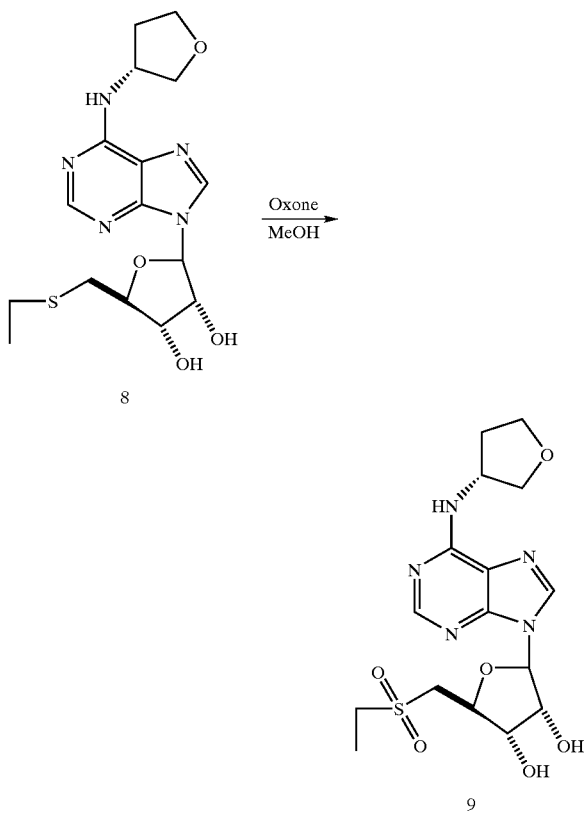

Scheme 5

This invention also includes pro-drugs of the $A_1$ agonist compositions of this invention. A pro-drug is a drug which has been chemically modified and may be biologically inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The compounds of this invention may be preferably modified at one or more of the hydroxyl groups to form pro-drugs. The modifications may be (1) ester or carbamate derivatives which may be cleaved by esterases or lipases, for example; (2) peptides which may be recognized by specific or non specific proteinase; or (3) derivatives that accumulate at a site of action through membrane selection or a pro-drug form or modified pro-drug form, or any combination of (1) to (3) above.

If a compound of this invention contains a basic group, then corresponding acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If a compound of this invention contains an acidic group, then corresponding cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

The compositions of this invention are useful for treating a variety of mammalian to disorders and preferably human disorders that are mediated by an $A_1$ adenosine receptor. For example, the compositions of this invention are useful for modifying cardiac activity in mammals experiencing a coronary electrical disorder that can be treated by stimulating an $A_1$ adenosine receptor. Examples of coronary electrical disorders that can be treated by the compositions of this invention include supraventricular tachycardias, atrial fibrillation, atrial flutter, and AV nodal re-entrant tachycardia. Furthermore, orally active $A_1$ agonists of this invention that demonstrate an excellent safety profile in treating supraventricular arrhythmias may also be used as a prophylactic for those at high risk of a myocardial ischemia.

The compositions of this invention are also useful for modifying adipocyte function by stimulating an $A_1$ adenosine receptor that leads to diminished release of NEFA and increased release of leptin. Disease states related to adipocyte function that can be modified using compositions of this invention include diabetes, and obesity.

In skeletal muscle cells, $A_1$ AdoR agonists mediate a synergistic stimulation of glucose uptake and transport by insulin (Vergauwen, L. et al, *J. Clin. Invest.* 1994, 93, 974–81; Challiss, R. A. et al, *Eur.J.Pharacol.*, 1992, 226, 121–8). Another therapeutic utility of compositions of this invention is more efficient regulation of glucose and a decrease of circulating levels of insulin in patients afflicted with diabetes.

The $A_1$ receptor agonist, R-PIA, has been shown to increase the leptin released from white adipocytes and augment insulin-stimulated leptin production (M. Ozeck Master's Thesis Univ. of Florida 1999 with L. Belardinelli). Evidence suggests that catecholamines inhibit the production of leptin from adipocytes through activation of β-adrenergic receptors. The anti-β-adrenergic effects of $A_1$ agonists on the adipocytes are believed to play a role in the increased release of leptin. The functional role of leptin is multifaceted including decreased appetite, stimulated energy utilization, and increased fertility.

The compositions of this invention may also be used to provide central nervous system neuroprotection by stimulating an $A_1$ adenosine receptor. Central nervous system disorders that may be treated using the compositions of this invention include epilepsy, and stroke.

In the kidney, there is evidence that stimulation of the $A_1$ AdoR promotes sodium retention, promotes exchange of sodium in urine for potassium, and reduces glomerular filtration rate as sodium excretion increases (Gellai, M. et al, *JPET,* 1998, 286, 1191–6; Wilcox, C. S. et al, *J.Am.Soc.Nephrol.,* 1999, 10, 714–720). It is believed that these responses are elicited by chronic local production of adenosine. That is, in the kidney there is a tonic effect of adenosine to stimulate the $A_1$ AdoR. Another clinical utility of compositions of this invention, therefore, is the selective antagonism of the $A_1$ AdoR in the kidney to inhibit sodium retention, inhibit the exchange of sodium for potassium, and preserve kidney glomerular filtration rate when sodium excretion rises to yield a potassium sparring diuretic that preserves renal function.

The compositions of this invention are further useful for providing cardiomyocyte protection from ischemic events by stimulating an $A_1$ adenosine receptor. Ischemic events treatable using the compositions of this invention include stable angina, unstable angina, cardiac transplant, and myocardial infarction.

An important aspect of compounds of this invention is that each compound has an intrinsic efficacy associated with it (for a discussion see T. P. Kenakin Stimulus Response Mechanisms. In Pharmacological Analysis of Drug-Receptor Interaction, Ed. Kenakin, T. P. New York: Raven Press, p 39–68). This intrinsic efficacy is not defined by it's affinity for the receptor, but it is defined as the quantitative effect of the compound to activate a given effector system (eg. cAMP production) in a given cell type. The intrinsic efficacy of a given compound may vary from cell type to cell type and/or from effector system to effector system. When a compound has an intrinsic efficacy lower than a full agonist (i.e. submaximal) than the agonist is called a partial agonist. Thus, a partial agonist is a molecule that binds to a receptor and elicits a response that is smaller than that of a full agonist (submaximal), but also competitively antagonizes the response(s) elicited by a full agonist. The tonic action of adenosine with respect to kidney function is a prime example where a partial $A_1$ agonist be expected to act as antagonists (e.g. adenosine). The tonic action of adenosine with respect to kidney function is a prime example where a partial $A_1$ agonist could be expected to act as an antagonist. The compounds of this invention are believed to have therapeutically useful affinities for the adenosine $A_1$ receptor, and they will have a range of intrinsic efficacies from full agonist to partial agonist. That is, some compounds may have no effect with respect to a given effector system in a given cell type, but be a full agonist in another cell type and/or effector system. The reason for such variable pharmacological behavior relates to the magnitude of the receptor reserve for the $A_1$ adenosine receptor in any given cell type (eg. AV nodal cells vs. adipocytes) and for a given response. The receptor reserve (spare receptor capacity) is the total number of receptors minus the fraction of receptors that is required to induce the maximal response using a full agonist (L. E. Limbird, Cell Surface Receptors: A Short Course on Theory and Methods, Kluwer Acad. Pub. 1996, Boston, Mass.). Therefore, the agonist could be a full agonist at eliciting a response, and a partial agonist for eliciting another response in other tissue or cells and still be an antagonist or lack activity for a third response in another tissue or cell. Consequently, a partial agonist targeted to a selected target is likely to cause fewer side effects than a full agonist. As a corollary, a full agonist elicits all the effects mediated by the respective receptor, whereas this is not necessarily the case of a partial agonist. The compounds of this invention based on their affinity for the $A_1$ receptor and their potency and selectivity to elicit $A_1$ receptor mediated responses have the potential for therapeutic intervention in the multiple disease states described above.

Partial $A_1$ agonists may have an added benefit for chronic therapy because they will be less likely to induce desensitization of the $A_1$ receptor (R. B. Clark, B. J. Knoll, R. Barber TiPS, Vol. 20 (1999) p. 279–286) and to cause side effects. Chronic administration of a full agonist (R-N6-phenylisopropyladenosine, R-PIA) for 7 days led to a desensitization of the $A_1$ receptor in terms of the dromotropic response in guinea pigs (note: a decrease in receptor number was observed—D. M. Dennis, J. C. Shryock, L. Belardinelli JPET, Vol. 272 (1995) p. 1024–1035). The $A_1$ agonist induced inhibitory effect on the production of cAMP by adenylate cyclase in adipocytes has been shown to desensitize upon chronic treatment with an $A_1$ agonist as well (W. J. Parsons and G. L. Stiles J. Biol. Chem. Vol. 262 (1987) p. 841–847).

The compositions of this invention may be administered orally, intravenously, through the epidermis, bolus, nasally, by inhalation or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples which follow serve to illustrate this invention. The Examples are not intended to limit the scope of this invention, but are provided to show how to make and use the compounds of this invention.

EXAMPLE 1

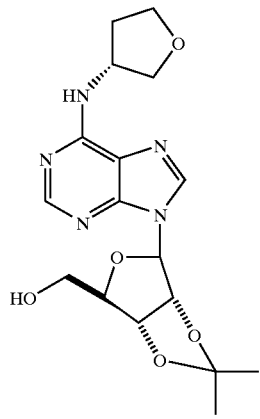

Intermediate-(4-{6-[((3R)oxolan-3-yl)amino]purin-9-yl} (1R, 2R, 5R)-7,7-dimethyl-3,6,8-trioxabicyclo[3.3.0]oct-2-yl)methan-1-ol (4)

To a solution of compound 3 (2.0 g, 6.0 mmol) and 2,2-dimethoxypropane (1.2 g, 11.8 mmol) in dimethylformamide (20 mL) was added p-toluenesulfonic acid (50 mg, 0.26 mmol) at 70° C. After 48 h at 70° C., the reaction was concentrated in vacuo to afford a solid. The solid was dissolved in methanol (3 mL), then triturated with ethyl ether (50 mL). The resultant crystals were collected by vacuum filtration to afford the intermediate 4.

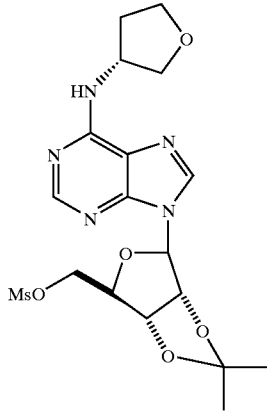

To a solution of 4 (190 mg, 0.5 mmol) in anhydrous pyridine (5 mL), was added MsCl (80 microL, 1 mmol) at 0° C. The reaction mixture was stirred at the same temperature for 2 h. Pyridine was removed under reduced pressure, residue was taken in dichloromethane (50 mL), washed with water (3×20 mL) and dried (Na$_2$SO$_4$). Evaporation of the solvent gave product 5 as a white foam: $^1$H NMR (CDCl$_3$) δ1.4 (s,3H), 1.6(s, 3H), 2.0–2.2(m, 1H), 2.3–2.5(m, 1H), 2.9(s, 3H), 3.7–4.2(m, 4H), 4.4–4.6(m, 3H), 4.8–5.0(bs, 1H), 5.1–5.2(bs, 1H), 5.4–5.5(bs, 1H), 6.1(s, 1H), 6.4–6.6 (bs, 1H), 8.1 (s, 1H), 8.4(s, 1H)

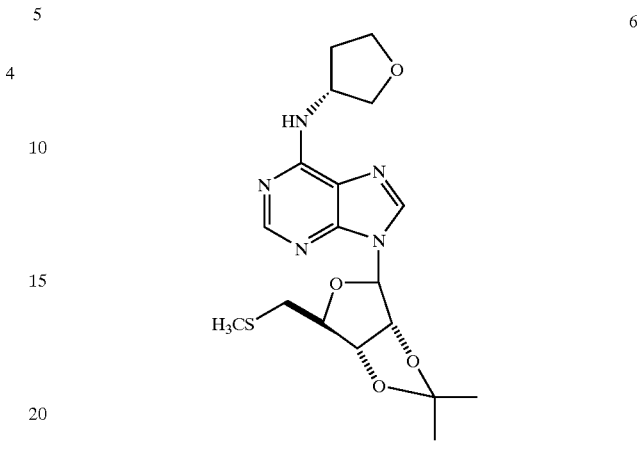

A mixture of mesylate 5 (150 mg) and methanethiolate(150 mg) in acetonitrile (2 mL) and water (1 mL) was heated at 70 C. for 24 h. The solvent was evaporated under reduced pressure and the residue was purified by preparative TLC [methanol-dichloromethane (1:19)] to afford product 6: $^1$H NMR (CDCl3) δ1.35 (s, 3H), 1.60 (s, 3H), 1.90–2.05 (m, 1H), 2.05 (s, 3H), 2.30–2.40 (m, 1H), 2.70 (doublet of AB quartet, 2H), 3.75–3.90 (m, 2H), 3.95–4.00 (m, 2H), 4.3–4.4 (m, 1H), 4.8–4.95 (m, 1H), 5.00–5.05 (m, 1H), 5.45–5.50 (d, 1H), 6.00–6.10 (m, 2H), 7.85 (s, 1H), 8.3 (s, 1H).

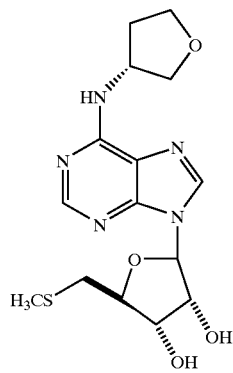

2-{6-[((3R)oxolan-3-yl)amino]purin-9-yl}(4S,5S,2R,3R)-5-(methylthiomethyl)oxolane-3,4-diol (7)

Compound 6 (50 mg) was dissolved in a mixture of acetic acid (8 mL) and water (2 mL) and heated at 90° C. for 16 h. Solvents were removed under reduced pressure, and the residue was purified by preparative TLC [methanol-dichloromethane (1:9)] to afford compound 7: 1H NMR (CDCl$_3$) δ1.90–2.05 (m, 1H), 2.15 (s, 3H), 2.30–2.40 (m, 1H), 2.75–2.85 (m, 2H), 3.80–3.90 (m, 2H), 3.90–4.00 (m, 2H), 4.30–4.45 (m, 2H), 4.50–4.55 (m, 1H), 4.75–4.95 (m, 1H), 5.90–5.95 (m, 1H), 6.30–6.60 (m, 1H), 7.95 (s, 1H), 8.25 (s, 1H).

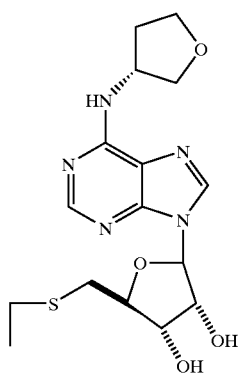

2-{6-[((3R)oxolan-3-yl)amino]purin-9-yl}(4S,5S,2R,3R)-5-[(Ethylthio)methyl]oxolan-3,4-diol(8)

Compound 8 was prepared in the manner similar to that of 7 substituting ethane thiolate for methane thiolate. (M+1)=382.30

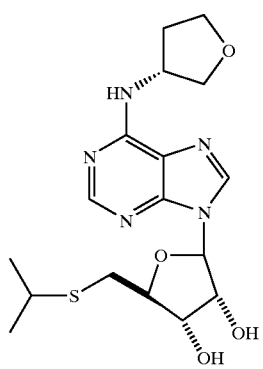

2-{6-[((3R)oxolan-3-yl)amino]purin-9-yl}(4S,5S,2R,3R)-5-[(Methylethylthio)methyl]oxolane-3,4-diol(10)

Compound 10 was prepared in the manner similar to that of 7 substituting i-propane thiolate for methane thiolate. $^1$H NMR (CDCl$_3$) δ1.25 (d, 6H), 1.90–2.05 (m, 1H), 2.15 (s, 3H), 2.30–240 (m, 1H), 2.85–2.87 (d, 2H), 2.95 (septet, 1H), 3.80–3.90 (m, 2H), 3.95–4.05 (m, 2H), 4.35–4.40 (m, 2H), 4.50–4.55 (m, 1H), 4.75–4.85 (m, 1H), 5.90–5.95 (d, 1H), 6.85–6.95 (m, 1H), 7.95 (s, 1H), 8.25 (s, 1H).

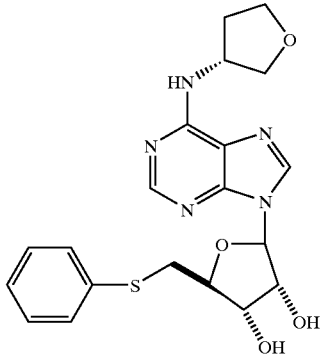

2-{6[((3R)oxolan-3-yl)amino]purin-9-yl}(4S,5S,2R,3R)-5-(phenylthiomethyl)oxolan-3,4-diol(11)

Compound 11 was prepared in the manner similar to that of 7 substituting phenyl thiolate for methane thiolate. $^1$H NMR (CDCl$_3$) 1.95–2.05 (m, 1H), 2.30–2.40 (m, 1H), 3.2 (d, 2H), 3.80–3.90 (m, 2H), 3.95–4.10 (m, 2H), 4.35–4.40 (d, 1H), 4.45 (t, 1H), 4.50–4.55 (m, 1H), 4.80–4.90 (m, 1H), 5.85 (d, 1H), 6.70–6.80 (m, 1H), 7.15–7.30 (m, 3H), 7.35 (d, 2H), 7.75 (s, 1H), 8.25 (s,1H).

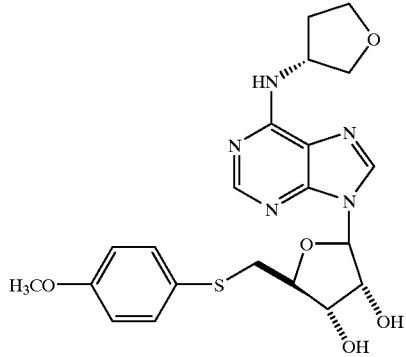

2-{6-[((3R)oxolan-3-yl)amino]purin-9-yl}(4S,5S,2R,3R)-5-[(4-Methoxyphenylthio)methyl]oxolane-3,4-diol(12)

This compound was prepared in the manner similar to that of 7 substituting 4-methoxyphenyl thiolate for methane thiolate. (M+1)=460.4

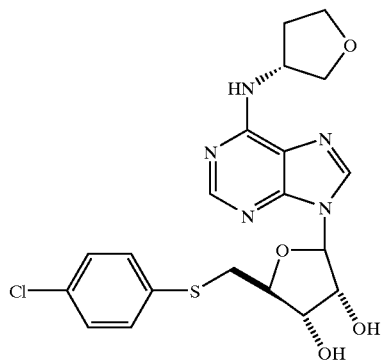

2-{6-[((3R)oxolan-3-yl)amino]purin-9-yl}(4S,5S,2R,3R)-5-[(4-chlorophenylthio)methyl]oxolane-3,4-diol(13)

This compound was prepared in a manner similar to that of 7 substituting 4-chlorophenyl thiolate for methane thiolate. (M+1)=464.3

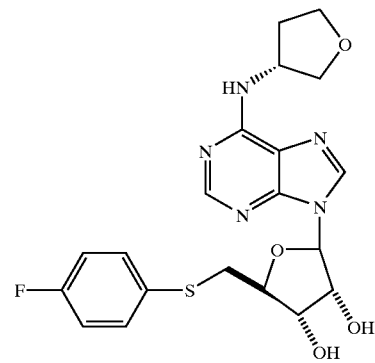

2-{6-[((3R)oxolan-3-yl)amino]purin-9-yl}(4S,5S,2R,3R)-5-[(4-fluorophenylthio)methyl]oxolane-3,4-diol(14)

This compound was prepared in a manner similar to that of 7 substituting 4-fluorophenyl thiolate for methane thiolate. (M+1)=448.3

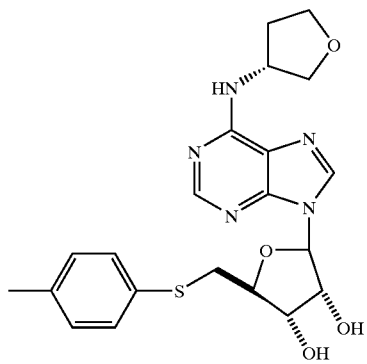

15

2-{6-[((3R)oxolan-3-yl)amino]purin-9-yl}(4S,5S,2R,3R)-5-[(4-methylphenylthio)methyl]oxolane-3,4-diol(15)

This compound was prepared in a manner similar to that of 7 substituting 4-methylphenyl thiolate for methane thiolate. (M+1)=444.38

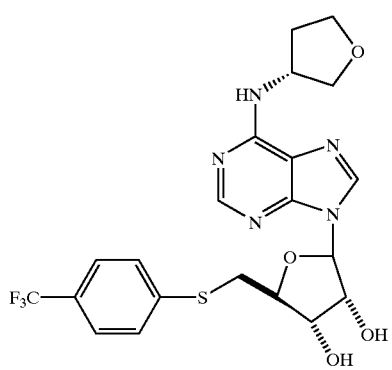

16

2-{6-[((3R)oxolan-3yl)amino]purin-9-yl}(4S,5S,2R,3R)-5-[(4-(trifluoromethyl)phenylthio)methyl]oxolane-3,4-diol (16)

This compound was prepared in a manner similar to that of 7 substituting 4-trifluoromethylphenyl thiolate for methane thiolate. (M+1)=488.36

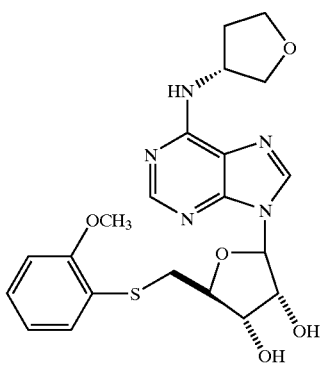

17

2-{6-[((3R)oxolan-3yl)amino]purin-9yl}(4S,5S,2R,3R)-5-[(2-Methoxyphenylthio)methyl]oxolane-3,4-diol(17)

This compound was prepared in a manner similar to that of 7 substituting 2-methoxyphenyl thiolate for methane thiolate. (M+1)=460.4

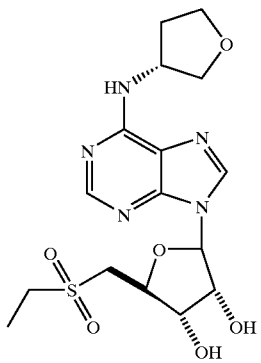

9

(5-{6-[((3R)oxolan-3-yl)amino]purinyl-9-yl}(2S,3S,4R,5R)-3,4-dihydroxyoxolan-2-yl)(ethylsulfonyl)methane(9)

To a cooled solution of sulfide 8 in methanol at 0° C. under nitrogen was added 3 eq. of Oxone (Potassium peroxy monosulfate) and the reaction mixture was allowed to stir at the same temperature for 1 hour. After the starting material consumed (by TLC), the reaction mixture was concentrated and filtered through a small plug of silica gel. Purification by preparative TLC [methanol-dichloromethane (1:19)] afforded 9 as an off-white hygroscopic solid. (M+1)=414.28

EXAMPLE 2

Binding Assays—$DDT_1$ Cells

Cell Culture

DDT cells (hamster vas deferens smooth muscle cell line) were grown as monolayers in petri dishes using Dulbecco's Modified Eagle's Medium (DMEM) containing 2.5 g ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of $1.2 \times 10^5$ cells per plate and experiments were performed 4 days later at approximately one day preconfluence.

Membrane Preparations

Attached cells were washed twice with HBSS (2×10 ml), scraped free of the plate with the aid of a rubber policeman in 5 ml of 50 mM Tris-HCl buffer pH 7.4 at 4° C. and the suspension homogenized for 10 s. The suspension was then centrifuged at 27,000×g for 10 min. The pellet was resuspended in homogenization buffer by vortexing and centrifuged as described above. The final pellet was resuspended in 1 vol of 50 mM Tris-HCl buffer pH 7.4 containing 5 mM $MgCl_2$ for $A_1$ AdoR assays. For the [$^{35}$S]GTPγS binding assay the final pellet was resuspended in 50 mM Tris-HCl pH 7.4 containing 5 mM $MgCl_2$, 100 mM NaCl and 1 mM dithiothreitol. This membrane suspension was then placed in liquid nitrogen for 10 min, thawed and used for assays. The protein content was determined with a Bradford™ Assay Kit using bovine serum albumin as standard.

Competitive Binding Assay

Pig striatum were prepared by homogenation in 50 mM Tris buffer ( 5×volume of tissue mass pH=7.4). After centrifugation at 19,000 rpm for 25 minutes at 4° C., the supernatant was discarded, and the process was repeated twice. Compositions of this invention were assayed to determine their affinity for the $A_1$ receptor in a pig striatum membrane prep or a $DDT_1$ membrane prep. Briefly, 0.2 mg of pig striatal membranes or DDT$_1$ cell membranes were treated with adenosine deaminase and 50 mM Tris buffer (pH=7.4) followed by mixing. To the branes was added 2 μL of serially diluted DMSO stock solution of the compounds of this invention at concentrations ranging from 100 microM to 10 nM. The control received 2 microL of DMSO alone, then the antagonist [$^3$H] 8-cyclopentylxanthine (CPX) for pig striatum or the agonist [$^3$H] 2-chloro-6-cyclopentyladenosine (CCPA) for DDT$_1$ membranes in Tris buffer (50 mM, pH of 7.4) was added to achieve a final concentration of 2 nM. After incubation at 23 C. for 2 h, then the solutions were filtered using a membrane harvester using multiple washing of the membranes (3×). The filter disks were counted in scintillation cocktail affording the amount of displacement of tritiated CPX or by the competitive binding compositions of this invention. Greater than a 5 point curve was used to generate Ki's and the number of experiments is indicated in the column marked in Table 1, below:

TABLE 1

| Compound # | K$_i$ - DDT$_1$ cell membrane | K$_i$ - Pig Striatum |
| --- | --- | --- |
| 7 | — | 222 nM |
| 10 | — | 188 nM |
| 11 | — | 44 nM |
| 12 | 820 nM | — |
| 14 | 363 nM | — |
| 15 | 922 nM | — |
| 16 | 7701 nM | — |
| 17 | 947 nM | — |

EXAMPLE 3

[$^{35}$S]GTPγS Binding Assays

A$_1$-agonist stimulated [$^{35}$S]GTPγS binding was determined by a modification of the method described by Giersckik et al. (1991) and Lorenzen et al. (1993). Membrane protein (30–50 μg) was incubated in a volume of 0.1 ml containing 50 mM Tris-HCl buffer pH 7.4, 5 mM MgCl$_2$, 100 mM NaCl, 1 mM dithiothreitol, 0.2 units ml$^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding was determined by the addition of 10 μM GTPγS. Agonist stimulated binding was determined as the difference between total binding in the presence of CPA and basal binding determined in the absence of CPA. Previous reports have shown that agonist stimulated [$^{35}$S]GTPγS binding was dependent on the presence of GDP (Gierschik et al., 1991; Lorenza et al., 1993; Traynor & Nahorski, 1995). In preliminary experiments, it was found that 10 μM GDP gave the optimal stimulation of CPA dependent [$^{35}$S]GTPγS binding and this concentration was therefore used in all studies. In saturation experiments, 0.5 nM [$^{35}$S]GTPγS was incubated with 0.5–1000 nM GTPγS. At the end of the incubation, each suspension was filtered and the retained radioactivity determined as described above. Results are presented normalized to the full agonist N-6-cyclopentyladenosine, CPA.

TABLE 2

| Compound # | GTP S |
| --- | --- |
| CPA | 100% |
| 8 | 104% |
| 12 | 52% |
| 13 | 69% |

TABLE 2-continued

| Compound # | GTP S |
| --- | --- |
| 14 | 61% |
| 15 | 48% |
| 16 | 31% |
| 17 | 52% |

EXAMPLE 4 cAMP Assay

A scintillation proximity assay (SPA) using rabbit antibodies directed at cAMP using an added tracer of adenosine 3',5'-cyclic phosphoric acid 2'-O-succinyl-3-[$^{125}$I] iodotyrosine methyl ester and fluoromicrospheres containing anti-rabbit specific antibodies as described by Amersham Pharmacia Biotech (Biotrak cellular communication assays). Briefly, DDT$_1$ cells were cultured in clear bottomed 96 well microtiter plates with opaque wells at concentrations between 10$^4$ to 10$^6$ cells per well in 40 μl of HBSS at 37° C. (5% CO$_2$ and 95% humidity). The partial of full A$_1$ agonists (5 μl) of this invention were incubated at various concentrations with the DDT$_1$ cells in the presence of rolipram (50 μM), and 5 μM forskolin for 10 min at 37° C. The cells were immediately lysed by treatment 5 μl of 10% dodecyltrimethylammonium bromide followed by shaking using microplate shaker. After incubation of the plate for 5 minutes, an immunoreagent solution (150 μl containing equal volumes of tracer, antiserum, and SPA fluoropheres) was added to each well followed by sealing the plate. After 15–20 h at 23° C., the amount of [$^{125}$I] cAMP to the fluoromicrospheres was determined by counting in a microtitre plate scintillation counter for 2 minutes. Comparison of counts with standard curves generated for cAMP using a similar protocol afforded the cAMP present after cell lysis. Results are presented normalized to the full agonist N-6-cyclopentyladenosine, CPA. Thus, the full agonist CPA diminished the amount of forskolin induced cAMP generation back to basal levels.

TABLE 3

| Compound # | cAMP |
| --- | --- |
| CPA | 107% |
| 8 | 37% |
| 12 | -9% |
| 13 | 30% |
| 14 | 47% |
| 15 | 22% |
| 16 | 22% |
| 17 | 18% |

What we claim is:

1. A compound of the formula:

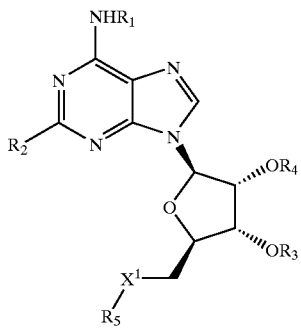

wherein:
- $R_1$ is tetrahydrofuran-3-yl;
- $R_2$ is hydrogen;
- $R_3$ and $R_4$ are hydrogen;
- $R_5$ is phenyl, optionally substituted with halo, alkyl of 1–5 carbon atoms, alkoxy of 1–5 carbon atoms, or trifluoromethyl; and
- $X^1$ is S;

or a pharmaceutically effective salt thereof.

2. The compound of claim 1 wherein $R_5$ is phenyl, namely 2-{6-[((3R)oxolan-3-yl)amino]purin-9-yl}(4S,5S,2R,3R)-5-(phenylthiomethyl)oxolane-3,4-diol.

3. The compound of claim 1 wherein $R_5$ is 4-methoxyphenyl, namely 2-{6-[((3R)oxolan-3-yl)amino]purin-9-yl}(4S,5S,2R,3R)-5-[(4-methoxyphenylthio)methyl]-oxolane-3,4-diol.

4. The compound of claim 1 wherein $R_5$ is 4-chlorophenyl, namely 2-{6-[((3R)oxolan-3-yl)amino]purin-9-yl}(4S,5S,2R,3R)-5-[(4-chlorophenylthio)methyl]oxolane-3,4-diol.

5. The compound of claim 1 wherein $R_5$ is 4-fluorophenyl, namely 2-{6-[((3R)oxolan-3-yl)amino]purin-9-yl}(4S,5S,2R,3R)-5-[(4-fluorophenylthio)methyl]-oxolane-3,4-diol.

6. The compound of claim 1 wherein $R_5$ is 4-trifluoromethyl, namely 2-{6-[((3R)oxolan-3-yl)amino]purin-9-yl}(4S,5S,2R,3R)-5-[(4-(trifluoromethyl)phenylthio)-methyl]oxolane-3,4-diol.

7. The compound of claim 1 wherein $R_5$ is 4-methylphenyl, namely, 2-{6-[((3R)oxolan-3-yl)amino]purin-9-yl}(4S,5S,2R,3R)-5-[(4-methylphenylthio)methyl]oxolane-3,4-diol.

8. The compound of claim 1 wherein $R_5$ is 2-methoxyphenyl, namely, 2-{6-[((3R)oxolan-3-yl)amino]purin-9-yl}(4S,5S,2R,3R)-5-[(2-methoxyphenylthio)methyl]oxolane-3,4-diol.

9. A method of stimulating an $A_1$ adenosine receptor, comprising administrating to a mammal in need thereof a therapeutically effective dose of a compound of claim 1 to the mammal.

10. The method of claim 9, wherein the mammal is a human.

11. The method of claim 9, wherein the therapeutically effective dose ranges from about 0.01 to about 100 mg/kg weight of the mammal.

12. A pharmaceutical composition comprising at least one pharmaceutically acceptable excipient and a therapeutically effective amount of a compound of claim 1.

13. A method of inhibiting supraventricular tachycardia, atrial fibrillation, atrial flutter, AV nodal re-entrant tachycardia, diabetes, cerebral ischemia, stroke, stable angina, unstable angina, or myocardial infarction, comprising administering a therapeutically effective amount of a compound of claim 1.

* * * * *